(12) United States Patent
Ogata

(10) Patent No.: US 12,733,888 B2
(45) Date of Patent: Sep. 15, 2026

(54) MEDICAL DEVICE, TABLE DRIVING METHOD, AND RECORDING MEDIUM

(71) Applicant: GE Precision Healthcare LLC, Wauwatosa, WI (US)

(72) Inventor: Kentaro Ogata, Hino (JP)

(73) Assignee: GE Precision Healthcare LLC, Wauwatosa, WI (US)

( * ) Notice: Subject to any disclaimer, the term of this patent is extended or adjusted under 35 U.S.C. 154(b) by 566 days.

(21) Appl. No.: 18/324,525

(22) Filed: May 26, 2023

(65) Prior Publication Data

US 2023/0380780 A1 Nov. 30, 2023

(30) Foreign Application Priority Data

May 30, 2022 (JP) ................................ 2022-088113

(51) Int. Cl.
*A61B 6/04* (2006.01)
*A61B 6/00* (2024.01)

(52) U.S. Cl.
CPC .......... *A61B 6/0487* (2020.08); *A61B 6/0407* (2013.01); *A61B 6/488* (2013.01); *A61B 6/547* (2013.01)

(58) Field of Classification Search
CPC ..... A61B 6/0487; A61B 6/0407; A61B 6/488; A61B 6/547; A61B 6/5276; A61B 6/0428; A61B 6/032; G06T 7/246; G06T 7/33
See application file for complete search history.

(56) References Cited

U.S. PATENT DOCUMENTS

| | | | | |
|---|---|---|---|---|
| 5,081,984 | A * | 1/1992 | Wess .................. | A61B 17/2255 601/4 |
| 2015/0366527 | A1* | 12/2015 | Yu ......................... | G06T 7/0012 600/407 |
| 2017/0165008 | A1* | 6/2017 | Finley .................. | A61B 6/4441 |
| 2017/0319155 | A1* | 11/2017 | Rubenstein ............ | A61B 6/107 |
| 2019/0069870 | A1* | 3/2019 | Igler ...................... | A61B 6/547 |

* cited by examiner

*Primary Examiner* — Justin C Mikowski
*Assistant Examiner* — Deborah Talitha Gedeon

(57) ABSTRACT

A medical device is described. The medical device includes a table and a processor. The processor executes operations including, driving the table based on an offset for correcting the table height positional offset to position the imaging location of a subject at a prescribed table height position, determining a center of gravity of the imaging location of the subject in the height direction of the table based on the medical image of the imaging location of the subject, calculating a difference between the prescribed position and the center of gravity as positional deviation of table height, and storing the positional deviation. The processor further executes operations including obtaining a representative value representing characteristics of the positional deviation distribution, determining whether the representative value of the positional deviation is statistically reliable, and updating the offset based on the representative value if the representative value is determined to be statistically reliable.

15 Claims, 20 Drawing Sheets

| Examination number | Examination location |
|---|---|
| #1 | Head |
| #2 | ↑ |
| #3 | ↑ |
| ⋮ | ⋮ |
| #a-1 | ↑ |
| #a | ↑ |
| #a+1 | Abdomen |
| #a+2 | ↑ |
| #a+3 | ↑ |
| ⋮ | ⋮ |
| #a+b-1 | ↑ |
| #a+b | ↑ |
| #a+b+1 | Chest |
| #a+b+2 | ↑ |
| #a+b+3 | ↑ |
| ⋮ | ⋮ |
| #a+b+c-1 | ↑ |
| #a+b+c | ↑ |

Fig. 3

| Imaging location | Offset (mm) |
|---|---|
| Abdomen | $F_1$ |
| Chest | $F_2$ |
| Head | $F_3$ |

| Examination number | Imaging location | Positional deviation d of table height |
|---|---|---|
| #1 | Head | $d_1$ |
| #2 | ↑ | |
| #3 | ↑ | |
| ⋮ | ⋮ | |
| #a-1 | ↑ | |
| #a | ↑ | |
| #a+1 | Abdomen | |
| #a+2 | ↑ | |
| #a+3 | ↑ | |
| ⋮ | ⋮ | |
| #a+b-1 | ↑ | |
| #a+b | ↑ | |
| #a+b+1 | Chest | |
| #a+b+2 | ↑ | |
| #a+b+3 | ↑ | |
| ⋮ | ⋮ | |
| #a+b+c-1 | ↑ | |
| #a+b+c | ↑ | |

Fig. 12

| Examination number | Imaging location | Positional deviation d of table height |
|---|---|---|
| #1 | Head | $d_1$ |
| #2 | ↑ | |
| #3 | ↑ | |
| ⋮ | ⋮ | |
| #a-1 | ↑ | |
| #a | ↑ | |
| #a+1 | Abdomen | |
| #a+2 | ↑ | |
| #a+3 | ↑ | |
| ⋮ | ⋮ | |
| #a+b-1 | ↑ | |
| #a+b | ↑ | |
| #a+b+1 | Chest | |
| #a+b+2 | ↑ | |
| #a+b+3 | ↑ | |
| ⋮ | ⋮ | |
| #a+b+c-1 | ↑ | |
| #a+b+c | ↑ | |

| Examination number | Imaging location | Positional deviation d of table height |
|---|---|---|
| #1 | Head | $d_1$ |
| #2 | ↑ | $d_2$ |
| #3 | ↑ | |
| ⋮ | ⋮ | |
| #a-1 | ↑ | |
| #a | ↑ | |
| #a+1 | Abdomen | |
| #a+2 | ↑ | |
| #a+3 | ↑ | |
| ⋮ | ⋮ | |
| #a+b-1 | ↑ | |
| #a+b | ↑ | |
| #a+b+1 | Chest | |
| #a+b+2 | ↑ | |
| #a+b+3 | ↑ | |
| ⋮ | ⋮ | |
| #a+b+c-1 | ↑ | |
| #a+b+c | ↑ | |

| Examination number | Imaging location | Positional deviation d of table height |
|---|---|---|
| #1 | Head | $d_1$ |
| #2 | ↑ | $d_2$ |
| #3 | ↑ | $d_3$ |
| ⋮ | ⋮ | ⋮ |
| #a-1 | ↑ | $d_{a-1}$ |
| #a | ↑ | |
| #a+1 | Abdomen | |
| #a+2 | ↑ | |
| #a+3 | ↑ | |
| ⋮ | ⋮ | |
| #a+b-1 | ↑ | |
| #a+b | ↑ | |
| #a+b+1 | Chest | |
| #a+b+2 | ↑ | |
| #a+b+3 | ↑ | |
| ⋮ | ⋮ | |
| #a+b+c-1 | ↑ | |
| #a+b+c | ↑ | |

| Imaging location | Offset (mm) |
| --- | --- |
| Abdomen | $F_1$ |
| Chest | $F_2$ |
| Head | ~~$F_3$~~ $d_{ave}$ (= D1) |

Fig. 17

| Examination number | Imaging location | Positional deviation d of table height |
|---|---|---|
| #1 | Head | $d_1$ |
| #2 | ↑ | $d_2$ |
| #3 | ↑ | $d_3$ |
| ⋮ | ⋮ | ⋮ |
| #a-1 | ↑ | $d_{a-1}$ |
| #a | ↑ | $d_a$ |
| #a+1 | Abdomen | $d_{a+1}$ |
| #a+2 | ↑ | $d_{a+2}$ |
| #a+3 | ↑ | $d_{a+3}$ |
| ⋮ | ⋮ | ⋮ |
| #a+b-1 | ↑ | $d_{a+b-1}$ |
| #a+b | ↑ | $d_{a+b}$ |
| #a+b+1 | Chest | |
| #a+b+2 | ↑ | |
| #a+b+3 | ↑ | |
| ⋮ | ⋮ | |
| #a+b+c-1 | ↑ | |
| #a+b+c | ↑ | |

| Examination number | Imaging location | Positional deviation d of table height |
|---|---|---|
| #1 | Head | $d_1$ |
| #2 | ↑ | $d_2$ |
| #3 | ↑ | $d_3$ |
| ⋮ | ⋮ | ⋮ |
| #a-1 | ↑ | $d_{a-1}$ |
| #a | ↑ | $d_a$ |
| #a+1 | Abdomen | $d_{a+1}$ |
| #a+2 | ↑ | $d_{a+2}$ |
| #a+3 | ↑ | $d_{a+3}$ |
| ⋮ | ⋮ | ⋮ |
| #a+b-1 | ↑ | $d_{a+b-1}$ |
| #a+b | ↑ | $d_{a+b}$ |
| #a+b+1 | Chest | $d_{a+b+1}$ |
| #a+b+2 | ↑ | $d_{a+b+2}$ |
| #a+b+3 | ↑ | $d_{a+b+3}$ |
| ⋮ | ⋮ | ⋮ |
| #a+b+c-1 | ↑ | $d_{a+b+c-1}$ |
| #a+b+c | ↑ | $d_{a+b+c}$ |

MEDICAL DEVICE, TABLE DRIVING METHOD, AND RECORDING MEDIUM

REFERENCE TO RELATED APPLICATIONS

This application claims priority to Japanese Application No. 2022-088113, filed on May 30, 2022, the disclosure of which is incorporated herein by reference in its entirety.

TECHNICAL FIELD

The present invention relates to a medical device including a table, a method of driving the table, and a recording medium on which instructions for controlling the medical device are recorded.

BACKGROUND ART

An X-ray Computed Tomography (CT) device is known as a medical device that noninvasively images a subject body. X-ray CT devices can capture images of an imaging location in a short period of time, and therefore have become widespread in hospitals and other medical facilities.

In recent years, imaging devices such as X-ray CT devices have been increasingly automated. For example, a technique for automatically driving a table so as to move a subject body to a prescribed position suitable for imaging has been researched and developed.

SUMMARY OF THE INVENTION

Automatic control of the table enables moving the subject body automatically to corresponding positions for each imaging protocol. Therefore, even if a medical institution such as a hospital examines a large number of subject bodies in a day for regular checkups, positioning of each of the subject bodies in the imaging location prescribed positions is feasible. Therefore, regardless of which subject body is to be examined, the imaging location can be positioned at a prescribed position, enabling the subject body to undergo a high-quality examination.

On the other hand, even with automatic positioning, the height of the table may deviate from the ideal position. This positional deviation is known to be dependent on the environment in which the automatic positioning is used, for example, at a hospital A there is dx (mm) deviation in the height of the table while at a different hospital B, there is dy (mm) (dy dx) deviation in the height of the table. Therefore, using positioning techniques to automatically move the table introduces hospital-specific positional offset in table height.

Also, depending on the imaging location, there may be a unique positional offset in the height of the table. For example, when the imaging location is the abdomen, the table height positional offset is within an allowable range, but when the imaging location is the head, the table height positional offset may be large.

Possible causes of table height positional offset include, for example, the thickness of cradle pads used in hospitals, the shape of accessories (for example, extenders), camera mounting positions, and camera calibration accuracy.

To address this table height positional offset, some current CT systems provide a minute adjustment function to table height positional offset to allow the operator to manually enter an offset to compensate for the table height positional offset. However, the offset value entered by the operator is, for example, the operator's own empirical value. Therefore, if the empirical value of the operator is not appropriate, there is a problem that the height of the table cannot be adjusted correctly.

Therefore, there is a need for a technique that can position the table height at a desired position.

A first aspect of the present invention is a medical device comprises a table on which a subject body is placed, and at least one processor, wherein each time an examination of a subject body is performed, the at least one processor executes operations including, driving the table using a table controller for controlling the table based on an offset for correcting the table height positional offset to enable positioning the imaging location of the subject body at a prescribed table height position, determining a center of gravity of the imaging location of the subject body in the height direction of the table based on the medical image of the imaging location of the subject body, and calculating a difference between the prescribed position and the center of gravity as positional deviation of table height, storing the positional deviation, and the at least one processor further executes operations including obtaining a representative value representing characteristics of the positional deviation distribution, determining whether the representative value of the positional deviation is statistically reliable, and updating the offset based on the representative value if the representative value is determined to be statistically reliable.

A second aspect of the present invention is a method of driving a table on which a subject body is placed and for each examination of the subject body, executing driving the table based on an offset for correcting the table height positional offset to enable positioning the imaging location of the subject body at a prescribed table height position, determining the center of gravity of the imaging location of the subject body in the height direction of the table based on a medical image of the imaging location of the subject body, calculating a difference between the prescribed position and a center of gravity as positional deviation of the table height, and storing the positional deviation. The method of driving the table further comprises obtaining a representative value indicating characteristics of the positional deviation distribution, determining whether the representative value of the positional deviation is statistically reliable, and updating the offset based on the representative value if the representative value is determined to be statistically reliable.

A third aspect of the present invention is a storing device, comprises a non-transitory computer-readable recording medium having stored thereon one or more instructions executable by at least one processor, and when executed by the at least one processor each time an examination of a subject body is executed, the one or more instructions for executing operations include driving a table using a table controller for controlling the table based on an offset for correcting the table height positional offset to enable positioning the imaging location of the subject body at a prescribed table height position, determining the center of gravity of the imaging location of the subject body in the height direction of the table based on a medical image of the imaging location of the subject body, calculating the difference between the prescribed position and the center of gravity as positional deviation of table height, and storing the positional deviation, and when executed by the one or more processors, the one or more instructions for executing operations further include obtaining a representative value representing characteristics of the positional deviation distribution, determining whether the representative value of the positional deviation is statistically reliable, and updating the offset based on the representative value if the representative value is determined to be statistically reliable.

Once the representative value of the table height positional deviation is sufficiently statistically reliable, the table height offset is updated based on the representative value. Therefore, when executing an examination of the next subject body, the table can be driven so that the height of the table is positioned based on the updated offset, enabling the imaging location to be positioned at or near the desired position.

BRIEF DESCRIPTION OF DRAWINGS

FIG. 3 is a diagram illustrating examination numbers #1 to #a+b+c and imaging locations examined at each examination number.

FIG. 6 is an explanatory diagram of offsets stored in a storage device.

FIG. 12 is a diagram illustrating the positional deviation d1 stored in association with an imaging location.

FIG. 17 is a diagram illustrating how the height offset of the table is updated from "F3" to "dave (=D1)" when imaging the head.

FIG. 18 is a diagram illustrating an examination flow of a subject body for examination number #a.

DESCRIPTION OF EMBODIMENTS

An embodiment for carrying out the invention will be described below, but the present invention is not limited to the following embodiment.

Figure 1:
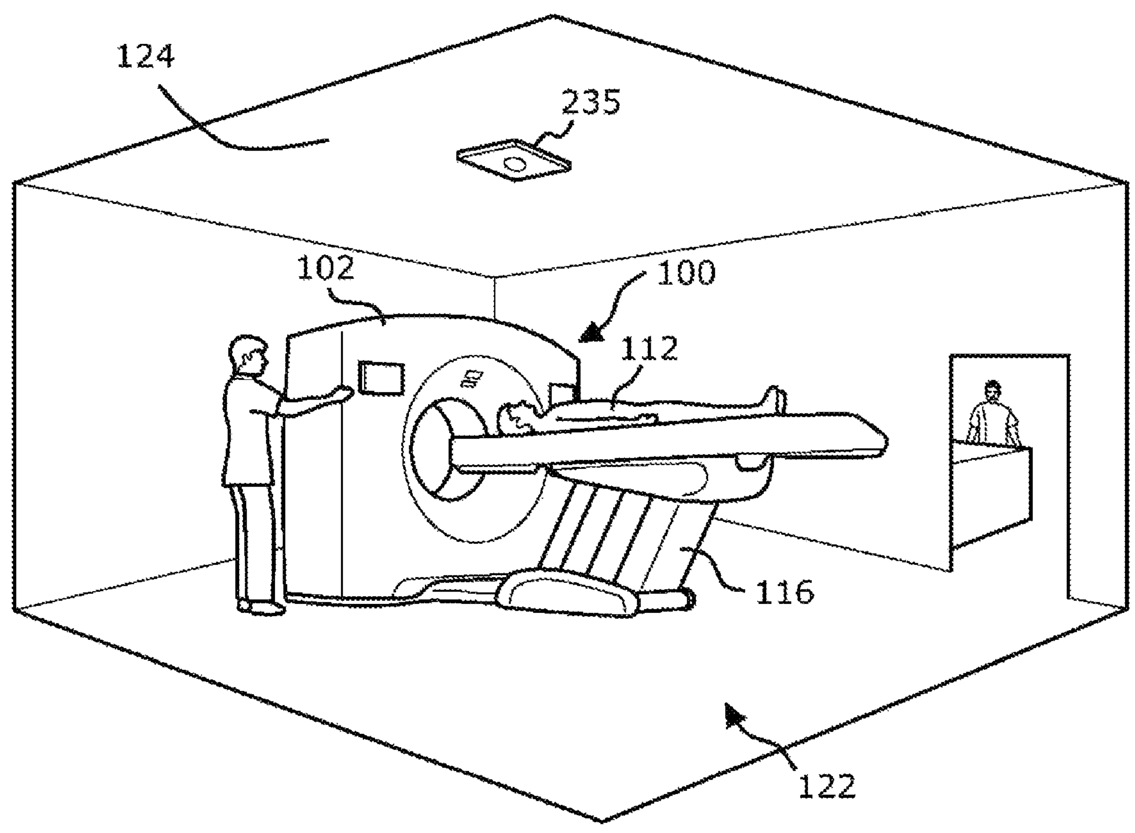
FIG. 1 is a perspective view of an X-ray CT device 100 of the present embodiment.
Figure 2:
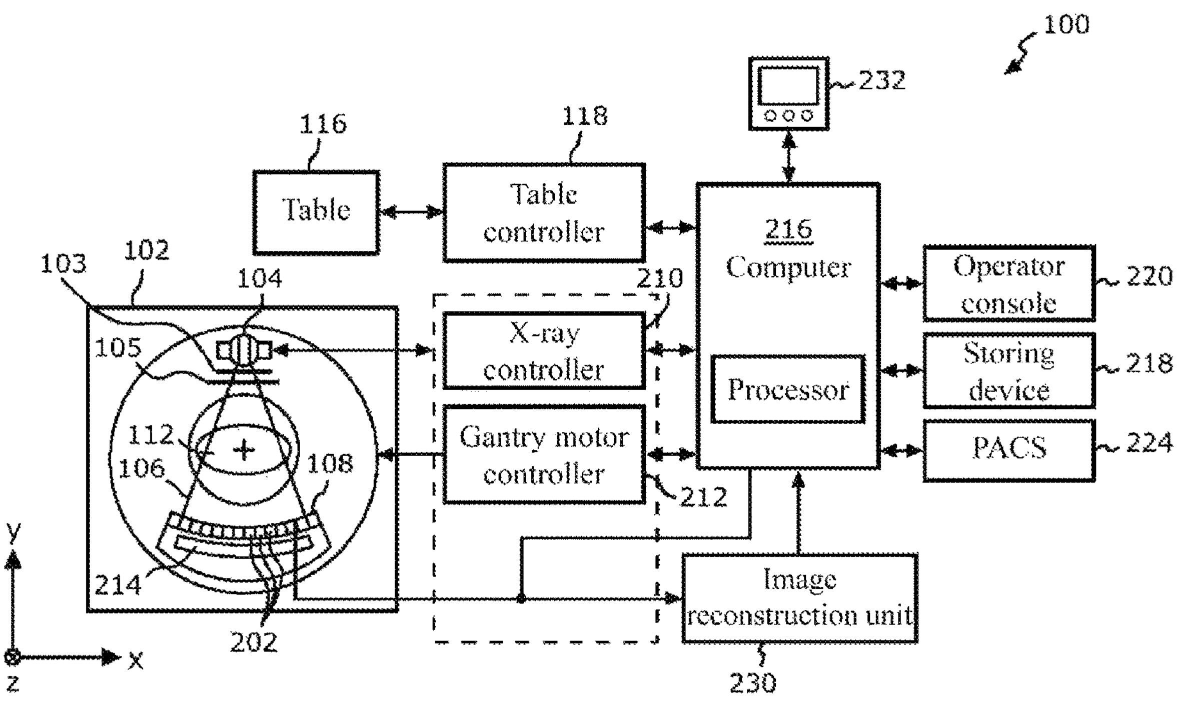
FIG. 2 is a block diagram of the X-ray CT device 100 of the present embodiment.

FIG. 1 is a perspective view of an X-ray CT device 100 of the present embodiment. FIG. 2 is a block diagram of the X-ray CT device 100 of the present embodiment. The X-ray CT device 100 includes a gantry 102 and a table 116. The gantry 102 and the table 116 are installed in a scan room 122. The gantry 102 has an opening 107 and a subject body 112 is transported through the opening 107 to scan the subject body 112. The gantry 102 is equipped with an X-ray tube 104, a filter part 103, a front collimator 105, and an X-ray detector 108.

The X-ray tube 104 generates X-rays when a prescribed voltage is applied to the cathode-anode tube. The X-ray tube 104 is configured to be rotatable on a path centered on the rotation axis within the XY plane. Here, the Z direction represents the body axis direction, the Y direction represents the vertical direction (the height direction of the table 116), and the X direction represents the direction perpendicular to the Z and Y directions. An X-ray tube compatible with a rapid kV switching system capable of switching the tube voltage may be provided as the X-ray tube 104. Moreover, in the present embodiment, although the X-ray CT device 100 includes one X-ray tube 104, two X-ray tubes may be included.

The filter part 103 includes, for example, a flat plate filter and/or a bow-tie filter. The front collimator 105 is a component that narrows the X-ray irradiation range so that X-rays are not emitted in unwanted areas. The X-ray detector 108 includes a plurality of detector elements 202. A plurality of detector elements 202 detect an X-ray beam 106 that is irradiated from the X-ray tube 104 and passes through the subject body 112, such as a patient. Thus, the X-ray detector 108 can acquire projection data for each view.

The projection data detected by the X-ray detector 108 is collected by the Data Acquisition System (DAS) 214. The DAS 214 performs prescribed processing, including sampling and digital conversion, on the collected projection data. The processed projection data is transmitted to a computer 216. Data from the DAS 214 may be stored in a storing device 218 by the computer 216. The storing device 218 includes one or more storage media that store programs as well as instructions to be executed by the processor. The storage medium can be, for example, one or more non-transitory, computer-readable storage media. Storage devices 218 may include, for example, hard disk drives, floppy disk drives, compact disc read/write (CD-R/W) drives, digital versatile disk (DVD) drives, flash drives, and/or solid state storage drives.

The computer 216 includes one or a plurality of processors. The computer 216 uses one or a plurality of processors to output commands and parameters to the DAS 214, X-ray controller 210, and/or gantry motor controller 212, to control system operations such as data acquisition and/or processing. In addition, the computer 216 uses one or more processors to execute signal processing, data processing, image processing, and the like in each step of the flow described below (see FIG. 4, FIG. 13, and FIG. 18).

An operator console 220 is linked to the computer 216. An operator can enter prescribed operator inputs related to the operation of the X-ray CT device 100 into the computer 216 by operating the operator console 220. The computer 216 receives operator input, including commands and/or scan parameters, via the operator console 220 and controls system operation based on that operator input. The operator console 220 can include a keyboard (not shown) or touch screen for the operator to specify commands and/or scan parameters.

The X-ray controller 210 controls the X-ray tube 104 based on control signals from the computer 216. In addition, a gantry motor controller 212 also controls the gantry motors to rotate structural elements such as the X-ray tube 104 and the X-ray detector 108 based on control signals from the computer 216.

FIG. 2 illustrates only one operator console 220, but two or more operator consoles may be linked to the computer 216. In addition, the X-ray CT device 100 may also allow a plurality of remotely located displays, printers, workstations, and/or similar devices to be linked via, for example, a wired and/or wireless network. In an embodiment, for example, the X-ray CT device 100 may include or be linked to a Picture Archiving and Communication System (PACS) 224. In a typical implementation, a PACS 224 may be linked to a remote system such as a radiology department information system, hospital information system, and/or internal or external network (not shown).

The computer 216 supplies commands to a table controller 118 to control the table 116. The table controller 118 can control the table 116 based on commands received. For example, the table controller 118 can drive the table 116 so that the subject body 112 is positioned appropriately for imaging.

As mentioned above, the DAS 214 samples and digitally converts the projection data acquired by the detector elements 202. The image reconstruction unit 230 then reconstructs the image using the sampled and digitally converted data. The image reconstruction unit 230 includes one or a plurality of processors, which can perform the image reconstruction process. In FIG. 2, the image reconstruction unit 230 is illustrated as a separate structural element from the computer 216, but the image reconstruction unit 230 may form a part of the computer 216. In addition, the computer 216 may also perform one or more functions of the image reconstruction unit 230. Furthermore, the image reconstruction unit 230 may be at a distance from the X-ray CT device 100 and operatively connected to the X-ray CT device 100 using a wired or wireless network. The computer 216 and image reconstruction unit 230 function as image generation devices.

The image reconstruction unit 230 can store the reconstructed image in the storage device 218. The image reconstruction unit 230 may also transmit the reconstructed image to the computer 216. The computer 216 can transmit the reconstructed image and/or patient information to a displaying device 232 communicatively linked to the computer 216 and/or image reconstruction unit 230.

The various methods and processes described in the present specification can be stored as executable instructions on a non-transitory storage medium within the X-ray CT device 100. The executable instructions may be stored on a single storage medium or distributed across a plurality of storage media. One or more processors provided in the X-ray CT device 100 execute the various methods, steps, and processes described in the present specifications in accordance with instructions stored on a storage medium.

A camera 235 is provided on a ceiling 124 of the scan room 122 as an optical image acquisition unit for acquiring an optical image in the scan room. Any optical image acquisition unit can be used as the optical image acquisition unit as long as it can image the surface of a subject such as a subject body. For example, a camera that uses visible light for imaging the subject, a camera that uses infrared for imaging the subject, or a depth sensor that uses infrared to acquire depth data of the subject and performs imaging of the surface of the subject based on the depth data, can be used as the optical image acquisition unit. Also, the optical image acquired by the optical image acquisition unit may be a 3D image or a 2D image. Furthermore, the optical image acquisition unit may acquire the optical image as a still image or as video. The X-ray CT device 100 is configured as described above.

In recent years, imaging devices such as X-ray CT devices have been increasingly automated. For example, a technique for automatically driving a table so as to move a subject body to a prescribed position suitable for imaging has been researched and developed.

Automatic control of the table enables moving the subject body automatically to corresponding positions for each imaging protocol. Therefore, even if a medical institution such as a hospital examines a large number of subject bodies in a day for regular checkups, positioning of each of the subject bodies in the imaging location prescribed positions is feasible. Therefore, regardless of which subject body is to be examined, the imaging location can be positioned at a prescribed position, enabling the subject body to undergo a high-quality examination.

On the other hand, even with automatic positioning, the table height position may deviate from the ideal position. The amount of this positional deviation has been found to depend on the environment in which the auto-positioning technique is being used, resulting in a hospital-specific positional offset of the table height.

To address this table height positional offset, some current CT systems provide a minute adjustment function to table height positional offset to allow the operator to manually enter an offset to compensate for the table height positional offset. However, the offset value entered by the operator is, for example, the operator's own empirical value. Therefore, if the empirical value of the operator is not appropriate, there is a problem that the height of the table cannot be adjusted correctly.

Therefore, in the present embodiment, a function is provided to automatically update the height offset of the table when the difference between the height at which the table is actually positioned and the ideal height of the table is large.

A flow of examining a subject body using the X-ray CT device of the present embodiment will be described below. In the present embodiment, for convenience of description, an example in which examinations are performed in order of examination numbers #1 to #a+b+c as indicated in FIG. 3 will be described. Examination numbers #1 to #a are for an imaging location of the "head," examination numbers #a+1 to #a+b are for an imaging location of the "abdomen," and examination numbers #a+b+1 to #a+b+c are for an imaging location of the "chest."

Figure 4:
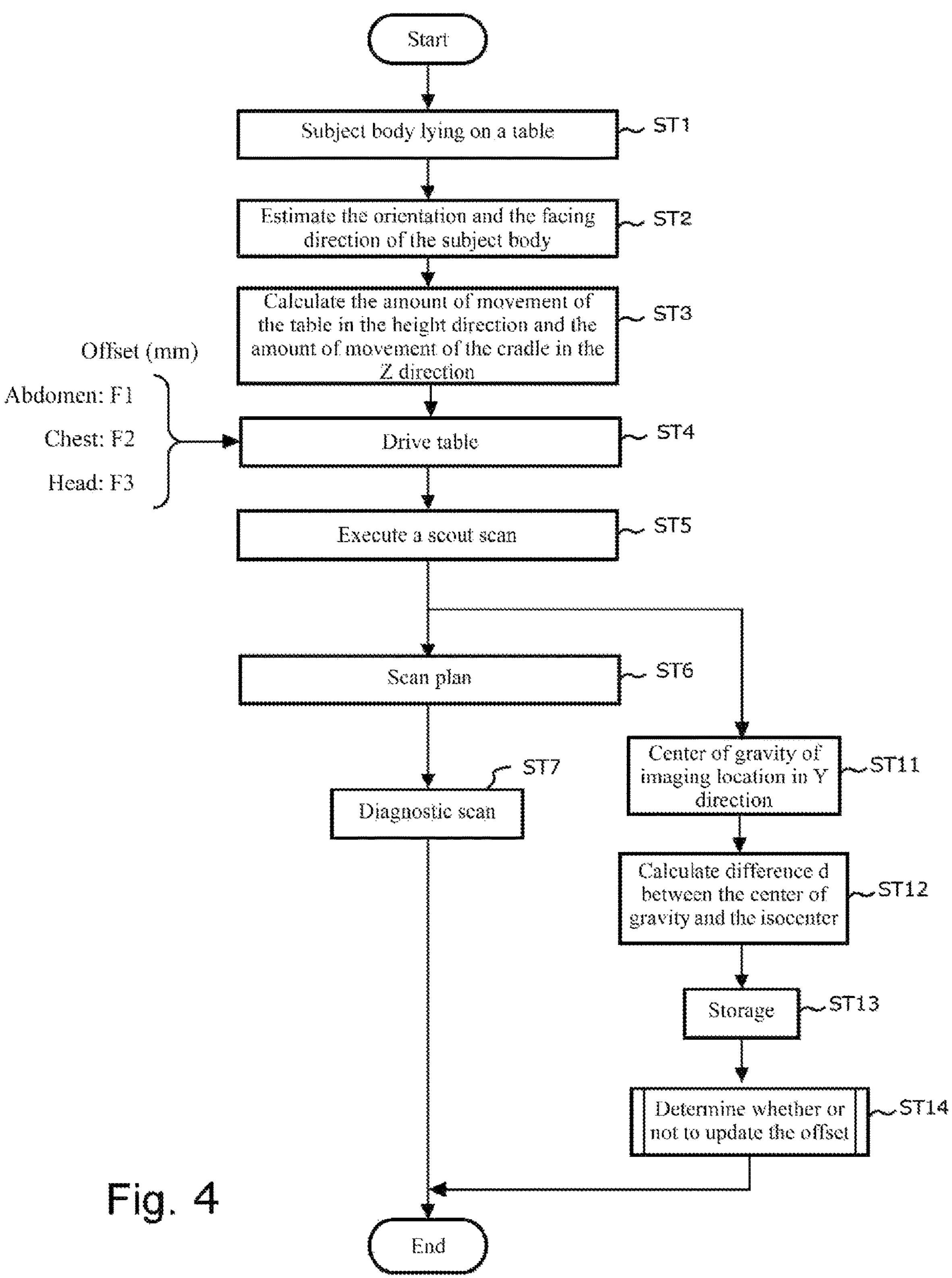
FIG. 4 is a diagram illustrating an example of an examination flow of a subject body.

FIG. 4 is a diagram illustrating an example of an examination flow of a subject body. Note that in executing the flow indicated in FIG. 4, some steps can be omitted or added, some steps can be divided into a plurality of steps, some steps can be executed in a different order, and some steps can be repeated.

First, an example of executing an examination of a subject body with examination number #1 will be described. The imaging location of examination number #1 is the head, as indicated in FIG. 3.

Figure 5:
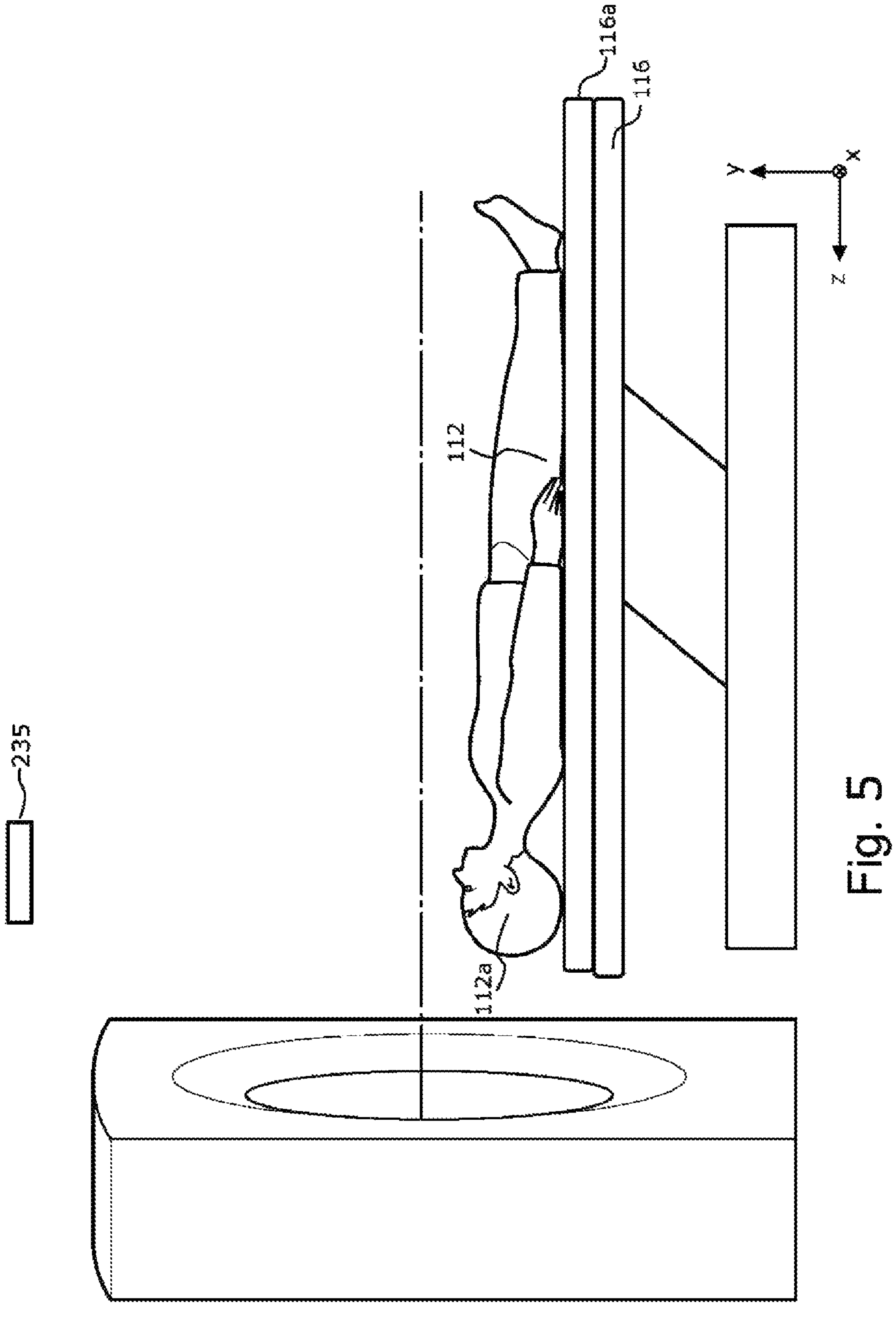
FIG. 5 is a diagram illustrating a subject body lying on a table.

In step ST1, the operator calls the subject body 112 into the scan room 122 and lays the subject body 112 on the table 116. FIG. 5 illustrates the subject body lying on the table 116.

The table 116 has a cradle **116*a* on which the subject body 112 is placed. The cradle 116*a*** is configured so as to be movable in the body axis direction (z direction).

The camera 235 starts imaging the table 116 and the surrounding area thereof before the subject body 112 enters the scan room 122. Signals captured by the camera 235 are sent to the computer 216. The computer 216 generates camera images (optical images) based on signals received from the camera 235. Camera images are stored in the storing device 218.

In step ST2, the computer 216 recognizes each part of the subject body (head, chest, abdomen, upper limbs, lower limbs, and the like) and the position of each part based on the camera image, and the orientation and the facing direction of the subject body on the table 116 are estimated. Here, the orientation of the subject body is, for example, supine position, lateral position, or prone position, and the facing direction of the subject body is HF (Head First), where the subject body is adjusted to move into the opening 107 of the gantry 102 starting with the head, or FF (Feet First) where the subject body is adjusted to move into the bore of the gantry starting with the lower limbs. For this estimation, for example, a deep learning method can be used.

In step ST3, the computer 216 calculates the amount of movement of the table 116 required to position the imaging location of the subject body at the scout scan start position based on the camera image. Specifically, based on the camera image, the computer 216 calculates the amount of movement of the table 116 in the Y direction (height direction of the table) and the amount of movement of the cradle in the z direction (body axis direction) required for positioning the imaging location of the subject body at the start position of the scout scan. After calculating the amount of movement, processing proceeds to step ST4.

In step ST4, the computer 216 causes the table controller 118 to drive the table 116 so that the imaging location is positioned at the scout scan start position. The table controller 118 drives the table 116 in consideration of both (1) and (2) below.

(1) The amount of movement of the table 116 in the height direction and the amount of movement of the cradle 116*a* calculated in step ST3.

(2) Offset for correcting height positional offset of the table 116. (2) is an offset for correcting the inherent positional offset of the height of the table 116 that occurs in each medical facility (for example, hospital). This offset is stored in a storage device (for example, storing device 218) for each imaging location. FIG. 6 is an explanatory diagram of offsets stored in the storage device. The offsets for type of imaging location set for each imaging location are indicated in the storing device. In FIG. 6, "abdomen," "thorax," and "head" are indicated as imaging locations. In addition, the height offsets of the table 116 for "abdomen," "chest," and "head" examinations are assumed to be "F1," "F2," and "F3." Offsets F1, F2, and F3 can be set to values within the range of 0 mm to several tens of mm, for example. Offsets F1, F2, and F3 are, for example, operator empirical values.

Figure 7:
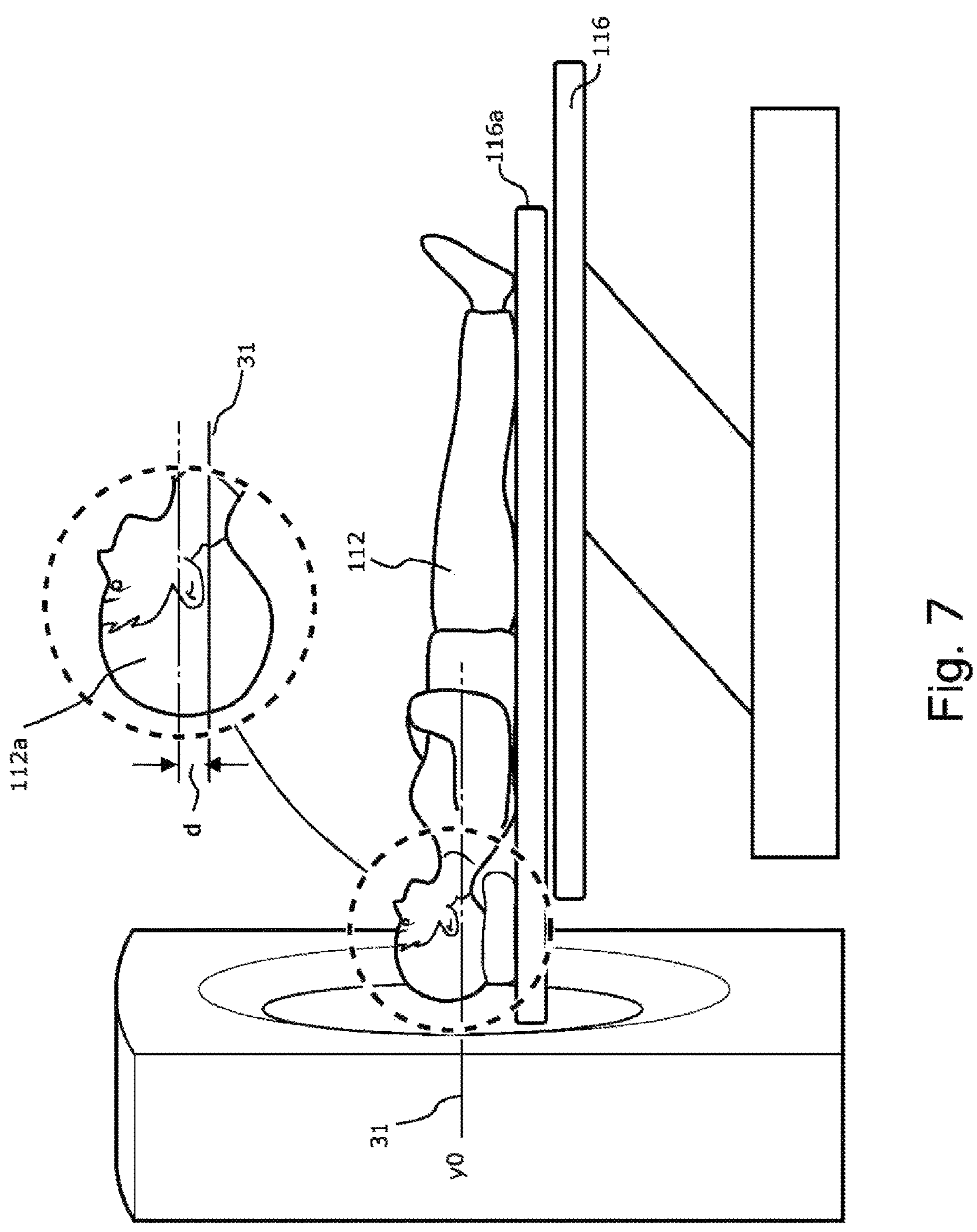
FIG. 7 is a diagram illustrating a state after driving the table.

The computer 216 selects the offset corresponding to the imaging location from among offsets F1, F2, and F3. Here, the imaging location is the head, so the computer 216 selects "F3" as the offset for correcting the inherent positional offset of the table 116 height. Therefore, the computer 216 drives the table 116 using the table controller 118 (see FIG. 2) to position the imaging location at the isocenter 31 (y coordinate: y0) based on the amount of movement of the table 116 in the height direction and the amount of movement of the cradle 116*a* calculated in step ST3, and the selected offset F3. FIG. 7 illustrates the state after driving the table 116 based on (1) and (2) described above. After driving the table 116, processing proceeds to step ST5.

Figure 8:
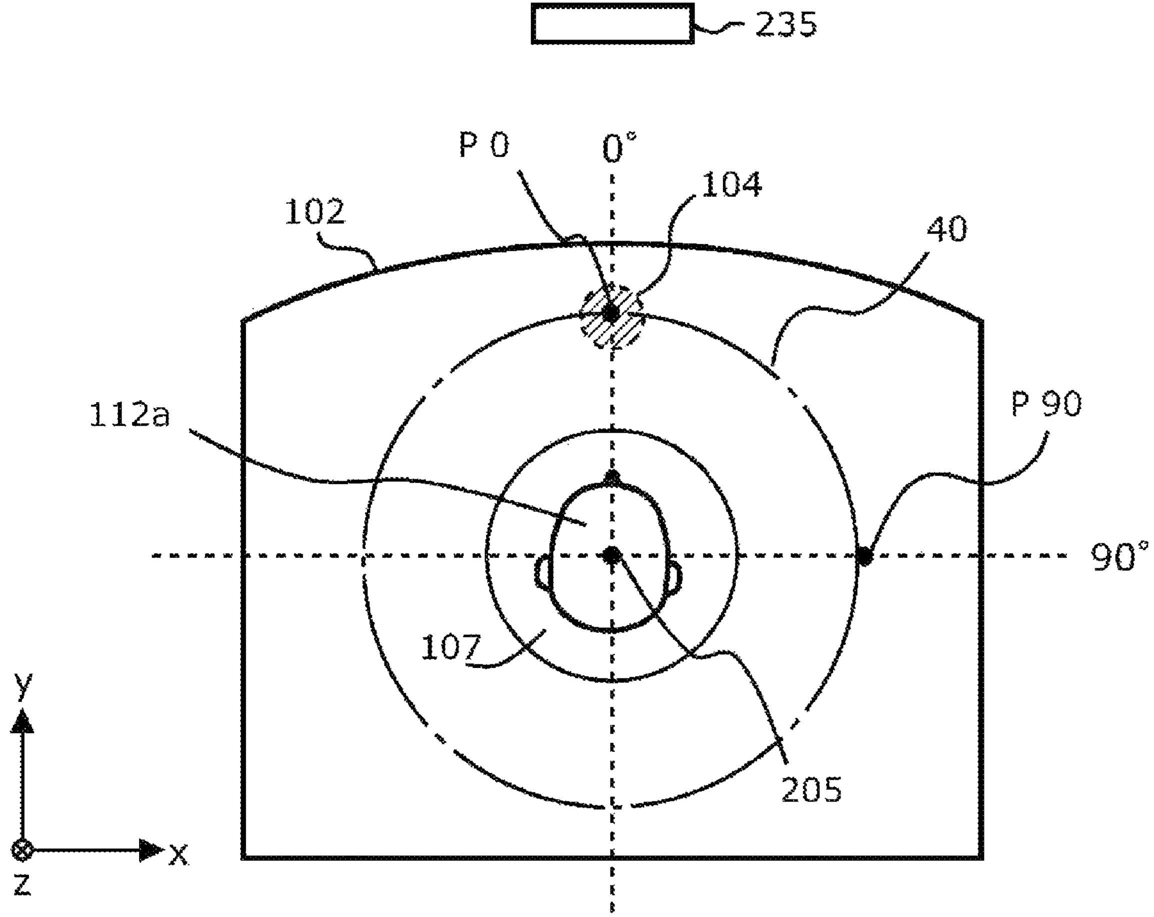
FIG. 8 is an explanatory diagram of a scout scan.

At step ST5, a scout scan of the subject body is executed. FIG. 8 is an explanatory diagram of the scout scan. A front view of the gantry 102 is illustrated in FIG. 8.

The gantry 102 includes an X-ray tube 104. The X-ray tube 104 is configured to be rotatable on a path 40 centered on the rotation axis 205 within the XY plane. The rotation axis 205 may be set so as to coincide with the isocenter 31, or may be set as the rotation axis 205 at a position deviated from the isocenter 31.

Note that FIG. 8 illustrates the head 112*a* of the subject body 112 relative to the opening 107 of the gantry 102 on the XY plane. Here, the imaging location is assumed to be the head 112*a*.

In the present embodiment, when executing a scout scan, the gantry motor controller 212 (see FIG. 2) controls the gantry motor so as to position the X-ray tube 104 at a position PO (angle 0°) on the path 40 directly above the rotation axis 205, as illustrated in FIG. 8. Furthermore, when the table controller 118 moves the cradle 116*a* in the Z direction, the X-ray controller 210 controls the X-ray tube 104 so as to irradiate X-rays.

The X-ray detector 108 (see FIG. 2) detects X-rays irradiated from the X-ray tube 104 and that pass through the subject body. The projection data detected by the X-ray detector 108 is collected by the DAS 214. The DAS 214 performs prescribed processing, including sampling, digital conversion, and the like, on the acquired projection data and transmits the data to the computer 216 or image reconstruction unit 230. On the computer 216 or image reconstruction unit 230, a processor reconstructs the image based on the data obtained from the scan.

Next, the X-ray tube 104 is rotated from 0° to 90°. Therefore, the X-ray tube 104 is positioned at a position of P90 (angle 90°). After the X-ray tube 104 is positioned at the position P90, X-rays are irradiated from the X-ray tube 104.

The X-ray detector 108 detects X-rays irradiated from the X-ray tube 104 and that pass through the subject body 112. The projection data detected by the X-ray detector 108 is collected by the DAS 214. The DAS 214 performs prescribed processing, including sampling, digital conversion, and the like, on the acquired projection data and transmits the data to the computer 216 or image reconstruction unit 230. On the computer 216 or image reconstruction unit 230, a processor reconstructs the image based on the data obtained from the scan.

Figure 9:
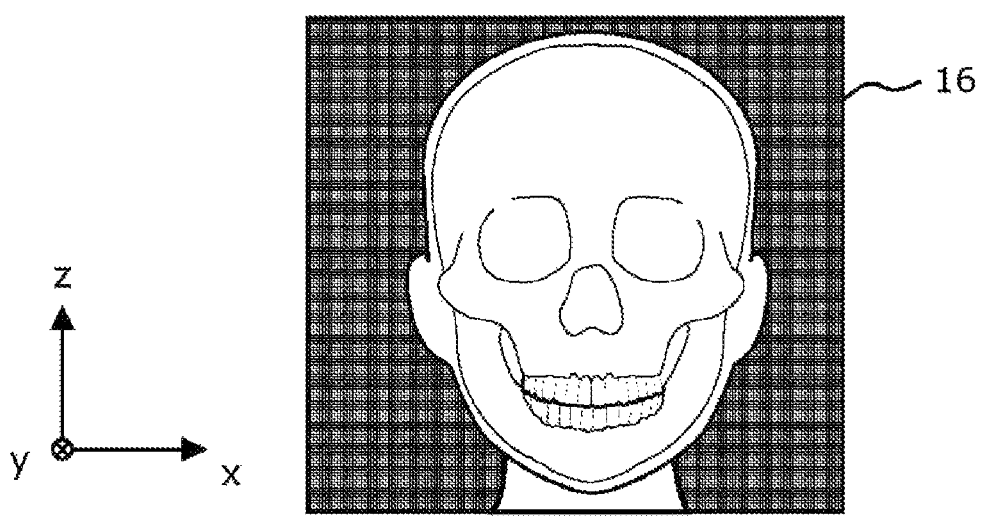
FIG. 9 is a schematic illustration of a scout image 16 when the X-ray tube 104 is positioned at an angle of 0° and a scout image 17 when the X-ray tube 104 is positioned at an angle of 90°.
Figure 9:
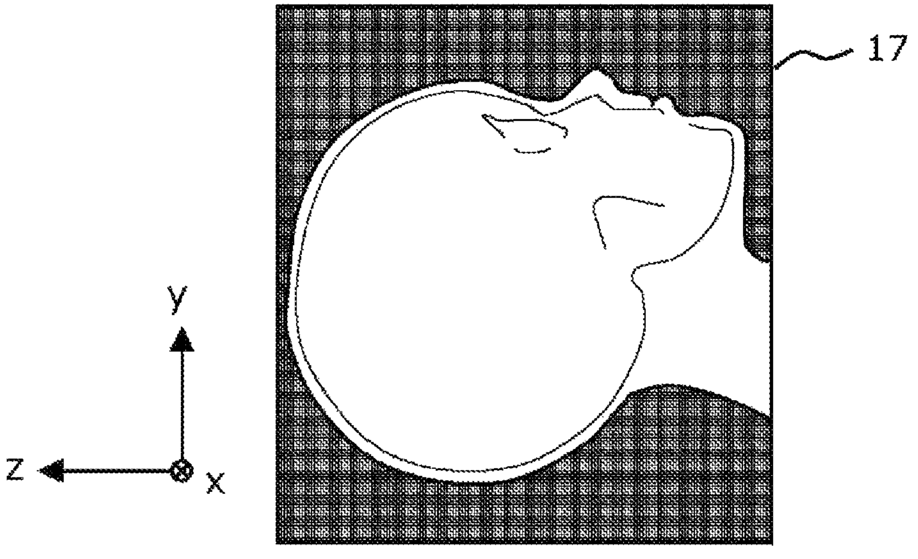

Therefore, by executing a scout scan, a scout image for when the X-ray tube 104 is positioned at an angle of 0° and a scout image for when the X-ray tube 104 is positioned at an angle of 90° can be reconstructed. FIG. 9 schematically illustrates a scout image 16 when the X-ray tube 104 is positioned at an angle of 0° and a scout image 17 when the X-ray tube 104 is positioned at an angle of 90°.

After executing the scout scan, processing proceeds to step ST6. At step ST6, the operator establishes a scan plan for a diagnostic scan. In the scan plan, the operator refers to the scout images 16 and 17 to set the scan range. After establishing the scan plan, processing proceeds to step ST7.

In step ST7, a diagnostic scan of the imaging location (head) is executed. The X-ray detector 108 detects X-rays irradiated from the X-ray tube 104 and that pass through the subject body 112. The projection data detected by the X-ray detector 108 is collected by the DAS 214. The DAS 214 performs prescribed processing, including sampling, digital conversion, and the like, on the acquired projection data and transmits the data to the computer 216 or image reconstruction unit 230. In the computer 216 or image reconstruction unit 230, a processor reconstructs a CT image necessary for diagnosis of the head of the subject body 112 based on data obtained from the diagnostic scan. The reconstructed CT image can be displayed on the displaying device 232.

While steps ST6 and ST7 are being executed, in steps ST11 to ST14, a determination is made as to whether or not the offset needs to be updated, and if necessary, updating the offset is executed. Steps ST11 to ST14 will be described below.

Figure 10:
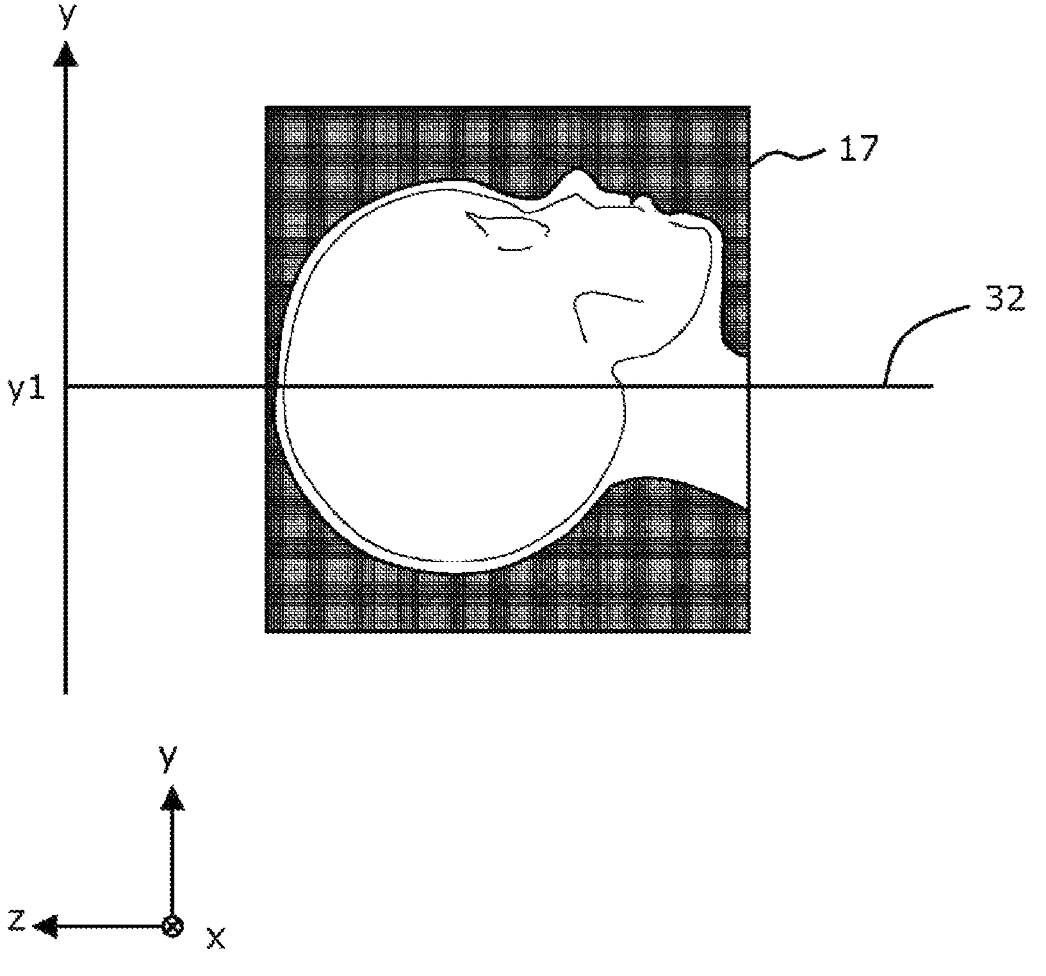
FIG. 10 is a diagram illustrating the center of gravity of the head in the Y direction.

In step ST11, the computer 216 obtains the center of gravity of the imaging location of the subject body in the Y direction (height direction of the table) based on the scout image 17 (see FIG. 9). In the present embodiment, the imaging location is the head, so the center of gravity of the head of the subject body in the Y direction is obtained. FIG. 10 indicates the center of gravity 32 of the head in the Y direction. In FIG. 10, the center of gravity 32 of the head in the Y direction is indicated by the Y-coordinate (y1). The center of gravity 32 is used as a baseline that serves as a reference for the positional deviation of the table 116 for the height direction in the next step ST12.

Figure 11:
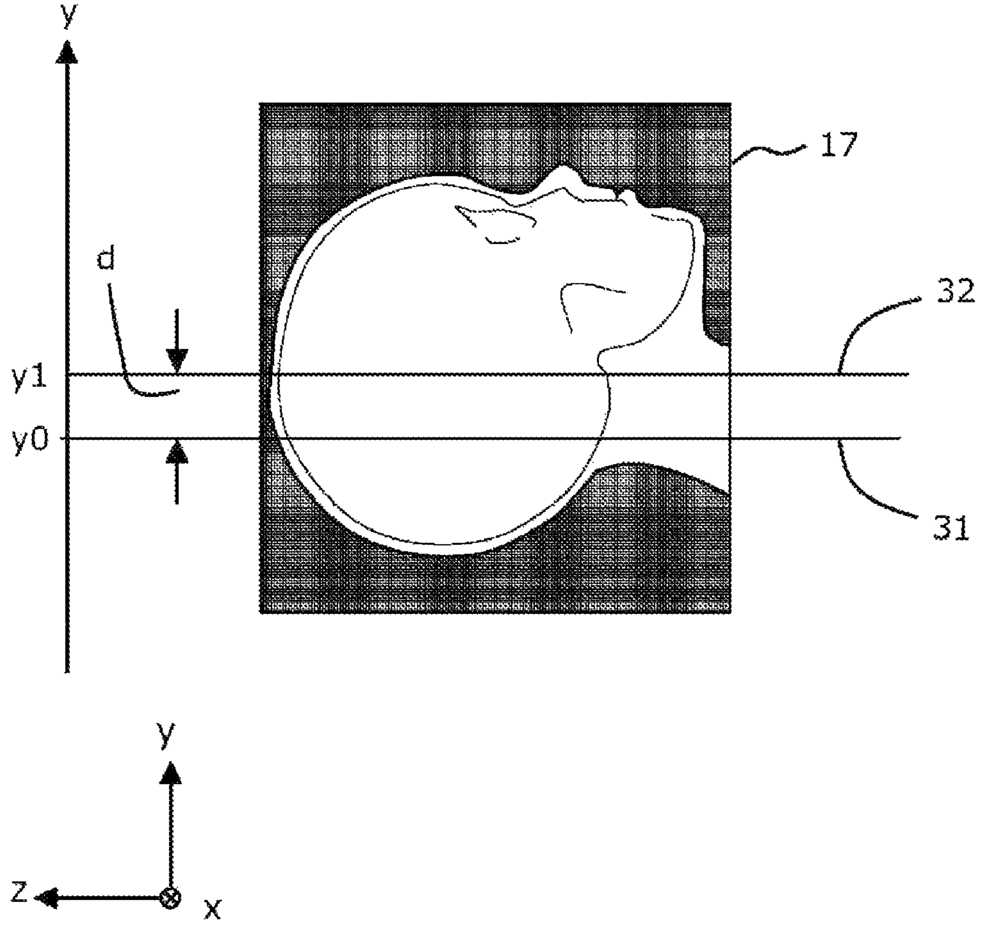
FIG. 11 is an explanatory diagram of the positional deviation of the height of the table.

In step ST12, as illustrated in FIG. 11, the computer 216 calculates a difference d between the isocenter 31 (Y coordinate: y0) and the center of gravity 32 (Y coordinate: y1) of the head in the Y direction obtained in step ST11. The computer 216 defines this difference d as the height positional deviation of the table 116. Here, it is assumed that the positional deviation d is $d=d_1$.

In step ST13, the computer 216 associates the positional deviation d with the examination number and the imaging location and stores it in the storage device, as illustrated in FIG. 12. Here, the positional deviation $d=d_1$ is stored associated with the examination number #1 and the imaging location (head). After storing the positional deviation d, processing proceeds to step ST14.

At step ST14, the computer 216 determines whether or not the offset F3 (see FIG. 4 and FIG. 6) for correcting the height positional offset of the table 116 needs to be updated. The determination method thereof will be described below.

Figure 13:
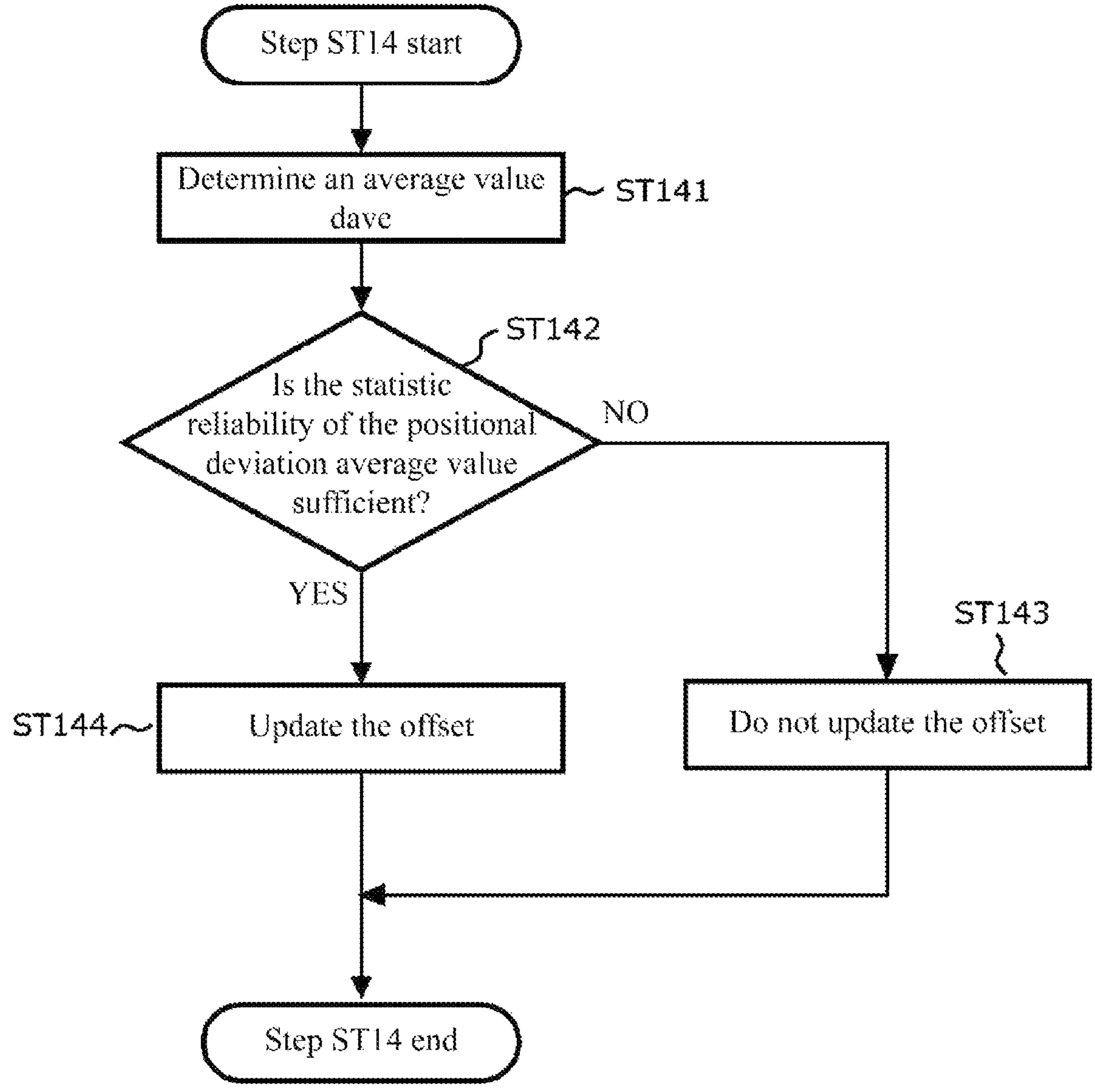
FIG. 13 is a diagram illustrating an example of the flow of step ST14.
Figure 14:
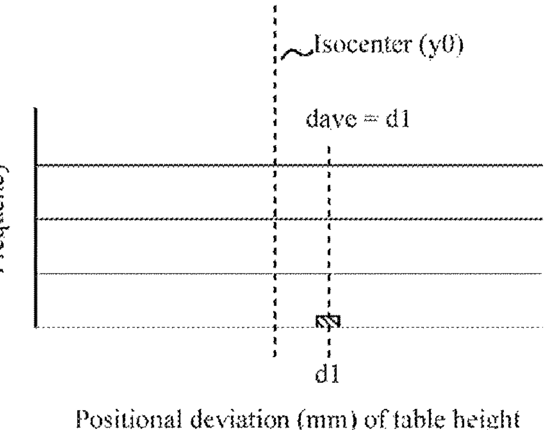
FIG. 14 is an explanatory diagram of step ST14.

FIG. 13 is a diagram illustrating an example of the flow of step ST14, and FIG. 14 is an explanatory diagram of step ST14.

The left side of FIG. 14 illustrates the positional deviation d in the height of the table 116 stored in the storage device, and the right side of FIG. 14 is a histogram of the positional deviation d in the height of the table 116.

In step ST141, the computer 216 calculates a representative value (central tendency) representing the characteristics of the positional deviation d distribution of the table 116 height. Representative values include, for example, the average value $d_{ave}$, the median value $d_{med}$, and the mode value $d_{mod}$. Here, the case of calculating the average value $d_{ave}$ as the representative value will be considered. Referring to FIG. 14, for the head, there is only one data point $d_1$ for the height positional deviation d of the table 116. Therefore, the average value is $d_{ave}=d_1$. After obtaining the average value $d_{ave}$, processing proceeds to step ST142.

At step ST142, the computer 216 determines whether the average value $d_{ave}=d_1$ is statistically reliable. Here, since the average value $d_{ave}=d_1$ is a value calculated from only one data point (that is, $d_1$), it is determined that the average value $d_{ave}=d_1$ is not statistically reliable. In this case, processing proceeds to step ST143 and the computer 216 determines to not update the offset F3, and the flow ends.

After the examination of the subject body using examination number #1 is completed, the next subject body with examination number #2 is examined. The imaging location of the subject body with examination number #2 is the head, like the imaging location of the subject body with examination number #1. The examination of the subject body of examination number #2 will be described below with reference to the flow of FIG. 4.

Figure 15:
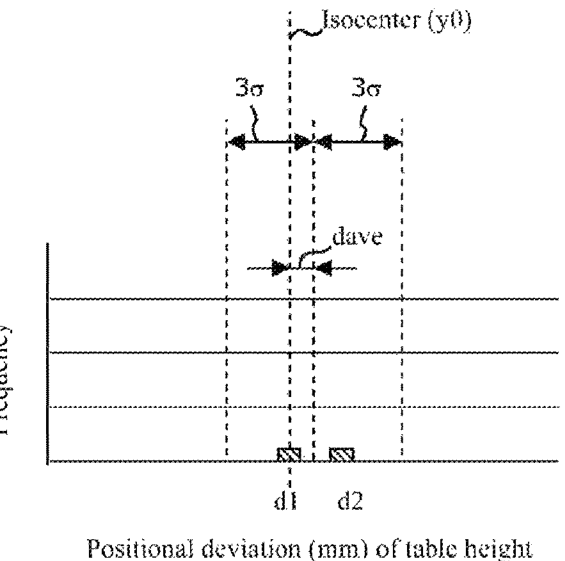
FIG. 15 is a diagram illustrating positional deviation d2 calculated for examination of the subject body for examination number #2.

Steps ST1 to ST5 are also executed in the examination of the subject body for examination number #2 in the same manner as in the examination of the subject body for examination number #1. Since the imaging location is the head, the table 116 is driven according to the offset F3 in step ST4. After driving the table 116, a scout scan (step ST5) is executed, a scan plan (step ST6) is established, and a diagnostic scan (step ST7) is executed. On the other hand, after the scout scan is executed in step ST5, the center of gravity in the Y direction of the imaging location (head) is determined (step ST11), the positional deviation d is determined (step ST12), and the positional deviation d is stored (step ST13). As illustrated in FIG. 15, the positional deviation d calculated for the examination of the subject body for examination number #2 is indicated by $d=d_2$. After storing the positional deviation $d_2$, processing proceeds to step ST14.

At step ST14, the computer 216 determines whether or not the offset F3 (see FIG. 4 and FIG. 6) for correcting the height positional offset of the table 116 needs to be updated. This determination method will be described below with reference to the flow of FIG. 13.

In step ST141, the computer 216 calculates the average value $d_{ave}$ of the height positional deviation d of the table 116. As illustrated in FIG. 15, the storage device stores positional deviation $d_1$ of the table 116 for the examination of the subject body for examination number #1 and positional deviation $d_2$ of the table 116 for the examination of the subject body for examination number #2. Therefore, the computer 216 calculates the average value $d_{ave}$ of the positional deviations $d_1$ and $d_2$. The average value $d_{ave}$ can be calculated using the following equation.

$$d_{ave}=(d_1+d_2)/2 \quad (1)$$

After obtaining the average value $d_{ave}$, processing proceeds to step ST142. At step ST142, the computer 216 determines whether the average value $d_{ave}$ (see equation (1)) is statistically reliable. In the present embodiment, the computer 216 calculates a threshold TH for determining whether the average value $d_{ave}$ is statistically reliable, and whether or not the average value $d_{ave}$ is statistically reliable is determined by determining whether or not the average value $d_{ave}$ satisfies the following equation (2) with respect to the threshold TH.

$$d_{ave} \geq TH \quad (2)$$

If the above equation (2) is satisfied, the computer 216 determines that the average value $d_{ave}$ is statistically reliable. Note that the threshold TH is a value calculated by the following equation using a standard deviation a representing the degree of variation in the positional deviation d.

$$TH=3\sigma \quad (3)$$

Therefore, in the present embodiment, the computer 216 determines whether or not the average value $d_{ave}$ is statistically reliable by determining whether or not the average value $d_{ave}$ satisfies the following equation (4).

$$d_{ave} \geq 3\sigma \quad (4)$$

If the equation (4) above is satisfied, the computer 216 determines that average value $d_{ave}$ is statistically reliable. Here, the average value $d_{ave}$ does not satisfy the above equation (4) because $d_{ave}<3\sigma$ as indicated in the histogram of FIG. 15. Therefore, processing proceeds to step ST143 and the computer 216 determines to not update the offset F3, and the flow indicated in FIG. 13 ends.

Similarly, every time the subject body is examined according to the flow indicated in FIG. 4 (and FIG. 13), in step ST13, the height positional deviation d of the table 116 is stored in association with the imaging location. Therefore, every time an examination of the subject body is executed, data of the height positional deviation d for the table 116 is accumulated for each imaging location.

Figure 16:
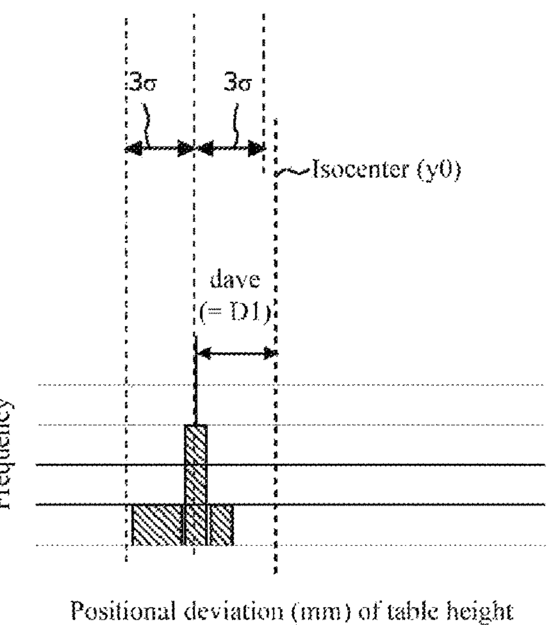
FIG. 16 is a diagram illustrating data of the height positional deviation d for the table accumulated by executing examinations for examination numbers #1 to #(a−1).

FIG. 16 is a diagram illustrating data of the height positional deviation d for the table accumulated by executing examinations for examination numbers #1 to #(a−1).

The imaging location for examination numbers #1 to #(a−1) is the head. Therefore, by executing the examinations with examination numbers #1 to #(a−1), data ($d_1$ to $d_a-1$) of the positional deviation d of the table 116 for the head is accumulated in the storing device. In step ST13, the computer 216 stores the positional deviation d ($=d_{a-1}$) of the table 116 height for examination number #(a−1), and then processing proceeds to step ST14.

At step ST14, the computer 216 determines whether or not the offset F3 (see FIG. 4 and FIG. 6) for correcting the height positional offset of the table 116 needs to be updated. This determination method will be described below with reference to the flow of FIG. 13.

In step ST141, the computer 216 calculates the average value $d_{ave}$ of the height positional deviation d of the table 116. As illustrated in FIG. 16, the storing device accumulates the positional deviations $d_1$ to $d_{a-1}$ of the table 116 height for examination numbers #1 to #(a−1). Therefore, the computer 216 calculates the average value $d_{ave}$ of the positional deviations $d_1$ to $d_{a-1}$. The average value $d_{ave}$ can be calculated using the following equation.

$$d_{ave}=(d_1+d_2+\ldots+d_{a-1})/(a-1)$$

Here, setting $(d_1+d_2+\ldots+d_{a-1})/(a-1)=D1$, gives $$d\text{ave}=D1 \quad (5)$$

After obtaining the average value $d_{ave}$ (=D1), processing proceeds to step ST142. At step ST142, the computer 216 determines whether the average value $d_{ave}$ (=D1) is statistically reliable based on equation (4). Here, the average value $d_{ave}$ (=D1) satisfies $d_{ave}\geq 3\sigma$ as indicated in FIG. 16. Therefore, the computer 216 determines to update the offset F3, and offset F3 is updated in step ST144. FIG. 17 is a diagram illustrating how the height offset of the table 116 is updated from "F3" to "$d_{ave}$ (=D1)" when imaging the head. After updating the offset, the flow indicated in FIG. 13 ends.

After the examination of the subject body for examination number #(a−1) is completed, the next subject body with examination number #a is examined.

Figure 18:
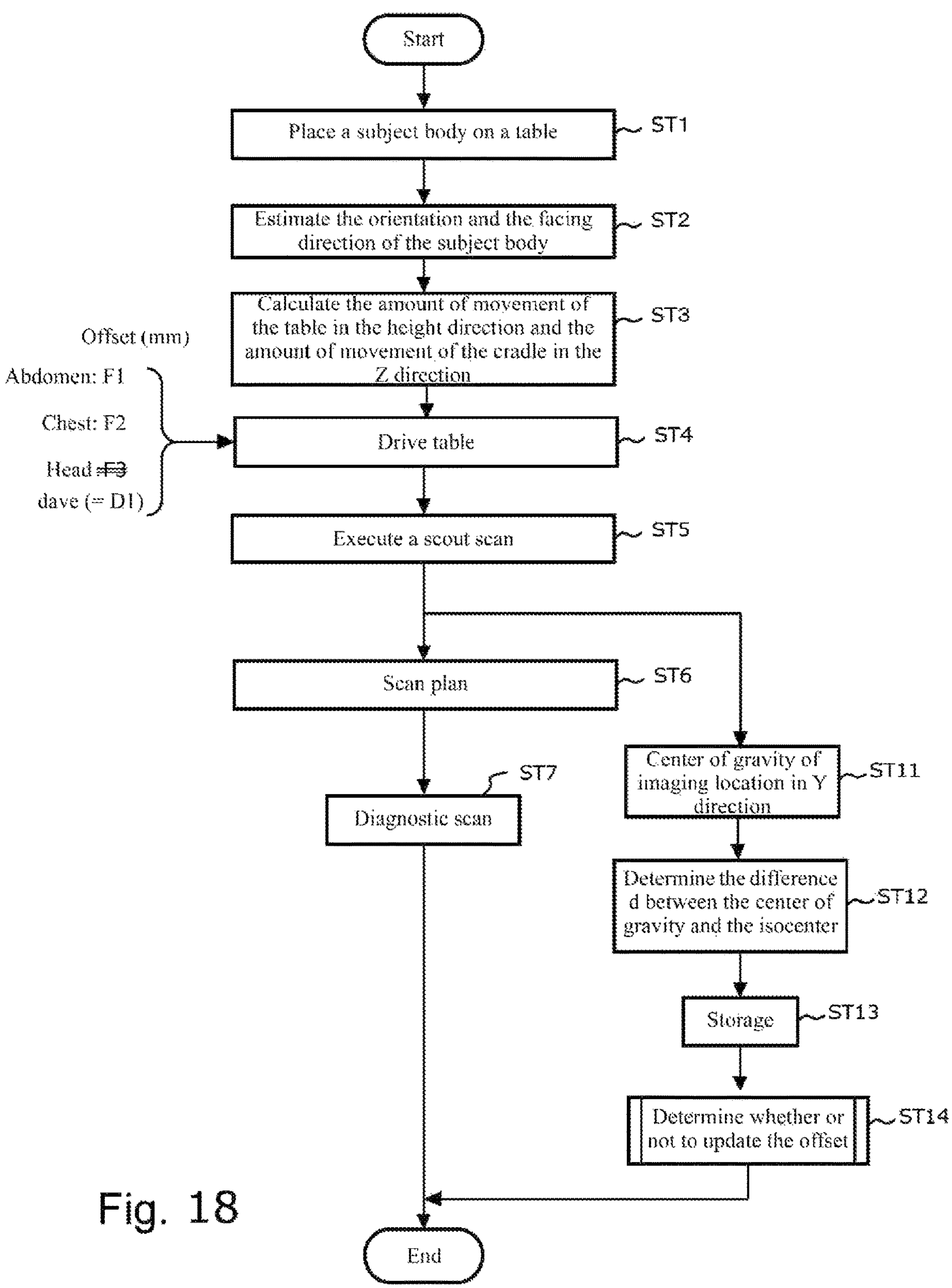

FIG. 18 is a diagram illustrating an examination flow of a subject body for examination number #a. The examination flow illustrated in FIG. 18 differs from the examination flow illustrated in FIG. 4 in that the offset used when the imaging location is the head is updated from "F3" to "$d_{ave}$ (=D1)" and is otherwise the same as the examination flow illustrated in FIG. 4.

The imaging location of the subject body with examination number #a is the head (see FIG. 16). Therefore, when executing the examination of the subject body with examination number #a, as illustrated in FIG. 18, the table 116 head offset "$d_{ave}$ (=D1)" is used in step ST4 and the examination of the head is executed.

As described above, in the examinations of the head for examination numbers #1 to #a−1, the average value $d_{ave}$ of the positional deviation d did not achieve statistical reliability and so the examinations were executed according to the flow in FIG. 4 with the table 116 height offset of F3 (mm). However, as illustrated in FIG. 16, the average value $d_{ave}$ (=D1) of the positional deviations $d_1$ to $d_{a-1}$ accumulated during examinations with examination numbers #1 to #a−1 was determined to be statistically reliable ($d_{ave}\geq 3a$), so the computer 216 updated the offset from F3 to $d_{ave}$ (=D1) (see FIG. 17). Therefore, in the next examination of the head of the subject body for examination number #a, the examination is executed according to the flow of FIG. 18 in which the table 116 height is offset by $d_{ave}$ (=D1). Therefore, in the examination of the head of the subject body for examination number #a, the scout scan can be performed with positioning the head at or near a desired position, thereby improving the quality of the examination.

Next, examinations of subject bodies for examination numbers #(a+1) to #(a+b) will be described. Examinations performed for examination numbers #(a+1) to #(a+b) are performed according to the flow illustrated in FIG. 18. Note that since the imaging location for examination numbers #(a+1) to #(a+b) is the abdomen, "F1" is used as the height offset of the table 116 in step ST4, while otherwise, examination flow is the same as that illustrated in FIG. 4. Therefore, in describing the flow illustrated in FIG. 18, mainly the differences from the flow in FIG. 4 will be described.

In step ST4, after driving the table 116 based on the offset "F1," a scout scan (step ST5) is executed, a scan plan (step ST6) is established, and a diagnostic scan (step ST7) is executed. On the other hand, after the scout scan is executed in step ST5, the center of gravity in the Y direction of the imaging location (abdomen) is determined (step ST11), the positional deviation d is determined (step ST12), and the positional deviation d is stored (step ST13). Therefore, every time an examination of the subject body is executed, data of the height positional deviation d for the table 116 is accumulated (see FIG. 19).

Figure 19:
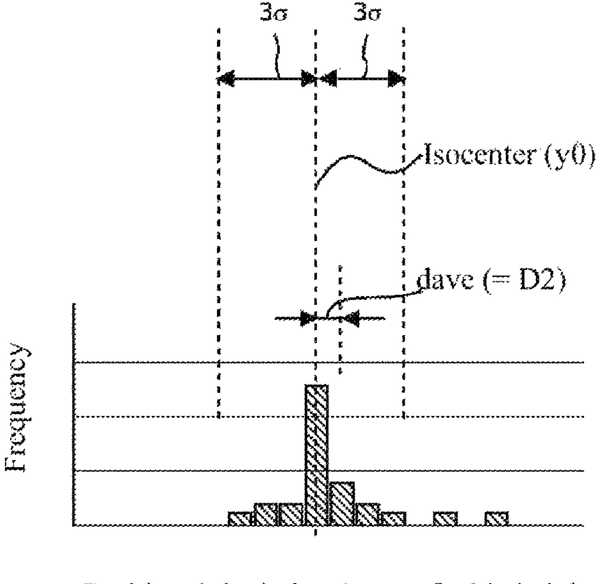
FIG. 19 is a diagram illustrating data of the height positional deviation d for the table accumulated by executing examinations for examination numbers #(a+1) to #(a+b).

FIG. 19 is a diagram illustrating data of the height positional deviation d for the table accumulated by executing examinations for examination numbers #(a+1) to #(a+b).

In the present embodiment, the imaging location for examination numbers #(a+1) to #(a+b) is assumed to be the abdomen. Therefore, by executing the examinations for the examination numbers #(a+1) to #(a+b), b data points ($d_a+1$ to $d_a+b$) of positional deviation d of the table 116 height for the abdomen are accumulated in the storing device. In step ST13, the computer 216 stores the positional deviation d ($=d_a+b$) of the table 116 height for examination number #(a+b), and then processing proceeds to step ST14.

At step ST14, the computer 216 determines whether or not the offset F1 (see FIG. 18) for correcting the height positional offset of the table 116 needs to be updated. This determination method will be described below with reference to the flow of FIG. 13.

In step ST141, the computer 216 calculates the average value $d_{ave}$ of the height positional deviation d of the table 116. As illustrated in FIG. 19, the storing device accumulates the positional deviations $d_{a+1}$ to $d_{a+b}$ of the table 116 height for examination numbers #(a+1) to #(a+b). Therefore, the computer 216 calculates the average value $d_{ave}$ of the positional deviations $d_{a+1}$ to $d_{a+b}$. The average value $d_{ave}$ can be calculated using the following equation.

$$d_{ave}=(d_{a+1}+d_{a+2}+\ldots+d_{a+b-1}+d_{a+b})/b$$

Here, setting $(d_{a+1}+d_{a+2}+\ldots+d_{a+b-1}+d_{a+b})/b=D2$, gives $$d_{ave}=D2 \quad (6)$$

After obtaining the average value $d_{ave}$, processing proceeds to step ST142. At step ST142, the computer 216 determines whether the average value $d_{ave}$ (=D2) is statistically reliable based on equation (4). Here, as illustrated in FIG. 19, the average value $d_{ave}$ (=D2) is $d_{ave}<3\sigma$ and so does not satisfy $d_{ave}\geq 3\sigma$. Therefore, the computer 216 determines that offset F1 does not need to be updated, and the flow illustrated in FIG. 18 ends.

Finally, examinations of subject bodies for examination numbers #(a+b+1) to #(a+b+c) will be described.

Examinations performed for examination numbers #(a+b+1) to #(a+b+c) are performed according to the flow illustrated in FIG. 18. Note that since the imaging location for examination numbers #(a+b+) [sic] to #(a+b+c) is the chest, “F2” is used as the height offset of the table 116 in step ST4, while otherwise, examination flow is the same as that illustrated in FIG. 4. Therefore, in describing the flow illustrated in FIG. 18, mainly the differences from the flow in FIG. 4 will be described.

In step ST4, after driving the table 116 based on the offset “F2,” a scout scan (step ST5) is executed, a scan plan (step ST6) is established, and a diagnostic scan (step ST7) is executed. On the other hand, after the scout scan is executed in step ST5, the center of gravity in the Y direction of the imaging location (chest) is determined (step ST11), the positional deviation d is determined (step ST12), and the positional deviation d is stored (step ST13). Therefore, every time an examination of the subject body is executed, data of the height positional deviation d for the table 116 is accumulated (see FIG. 20).

Figure 20:
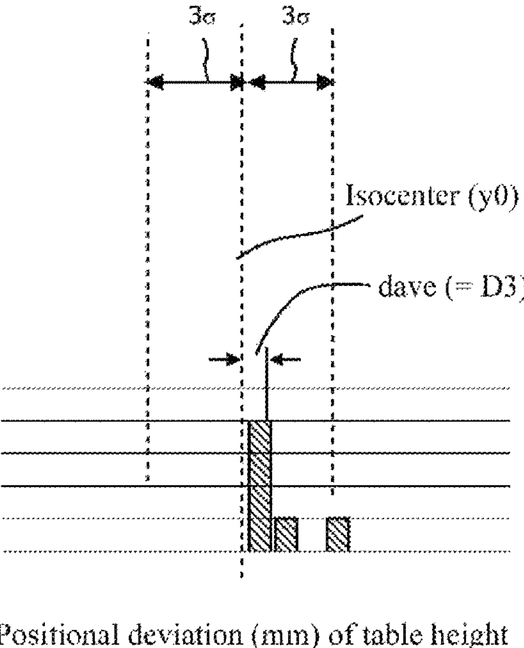
FIG. 20 is a diagram illustrating data of the height positional deviation d for the table accumulated by executing examinations for examination numbers #(a+b+1) to #(a+b+c).

FIG. 20 is a diagram illustrating data of the height positional deviation d for the table accumulated by executing examinations for examination numbers #(a+b+1) to #(a+b+c).

In the present embodiment, the imaging location for examination numbers #(a+b+1) to #(a+b+c) is assumed to be the chest. Therefore, by executing the examinations for the examination numbers #(a+b+1) to #(a+b+c), c data points ($d_a$+b+1 to $d_a$+b+c) of positional deviation d of the table 116 height for the chest are accumulated in the storing device. In step ST13, the computer 216 stores the positional deviation d (=$d_a$+$_b$+c) of the table 116 height for examination number #(a+b+c), and then processing proceeds to step ST14.

At step ST14, the computer 216 determines whether or not the offset F2 (see FIG. 18) for correcting the height positional offset of the table 116 needs to be updated. This determination method will be described below with reference to the flow of FIG. 13.

In step ST141, the computer 216 calculates the average value $d_{ave}$ of the height positional deviation d of the table 116. As illustrated in FIG. 20, the storing device accumulates the positional deviations $d_{a+b+1}$ to $d_{a+b+c}$ of the table 116 height for examination numbers #(a+b+1) to #(a+b+c). Therefore, the computer 216 calculates the average value $d_{ave}$ of the positional deviations $d_{a+b+1}$ to $d_{a+b+c}$. The average value $d_{ave}$ can be calculated using the following equation.

$$d_{ave}=(d_{a+b+1}+d_{a+b+2}+\ldots+d_{a+b+c-1}+d_{a+b+c})/c$$

Here, setting $(d_{a+b+1}+d_{a+b+2}+\ldots+d_{a+b+c-1}+d_{a+b+c})/c$=D3, gives $$d_{ave}=D3 \tag{7}$$

After calculating the average value $d_{ave}$ (=D3), processing proceeds to step ST142.

At step ST142, the computer 216 determines whether the average value $d_{ave}$ (=D3) is statistically reliable based on equation (4). Here, as illustrated in FIG. 20, the average value $d_{ave}$(=D3) is $d_{ave}<3\sigma$ and so does not satisfy $d_{ave}\geq 3\sigma$. Therefore, the computer 216 determines that offset F2 does not need to be updated, and the flow illustrated in FIG. 18 ends. In this manner, examinations with examination numbers #1 to #a+b+c are executed.

In the present embodiment, data for the height positional deviation d of the table 116 are accumulated for each imaging location, and when the average value $d_{ave}$ of the positional deviation d satisfies $d_{ave}\geq 3a$ (see equation (4)), the offset can be updated automatically. Therefore, the operator of the X-ray CT device does not have to manually change the offset, so the workload of the operator can be reduced. In addition, in the present embodiment, even if accessories such as pads or the like are replaced, repeatedly executing examinations of subject bodies with the X-ray CT device enables automatic adjustment for the unique positional offset of the table height caused by the accessory.

In addition, in the present embodiment, since the average value $d_{ave}$ of the positional deviation is calculated for each imaging location, the positional offset of the table 116 height can be adjusted for each imaging location.

In the present embodiment, the offset is automatically updated based on dave≥3σ (see equation (4)). However, the offset may be automatically updated based on a conditional expression other than $d_{ave}\geq 3\sigma$. For example, instead of $d_{ave}\geq 3\sigma$, the offset may be automatically updated when $d_{ave}\geq 2\sigma$ is satisfied.

In the present embodiment, the average value $d_{ave}$ of the positional deviation is used to determine whether or not to update the offset. However, instead of the average value $d_{ave}$, other representative values such as the median value $d_{med}$ or the mode value $d_{mod}$ may be used to determine whether or not to update the offset.

In the present embodiment, the threshold TH is calculated using the standard deviation a (see equation (3)). However, instead of the standard deviation a, another index such as variance may be used to calculate the threshold TH.

In the present embodiment, the positional deviation d is defined with reference to the isocenter 31. However, the positional deviation d may be defined with reference to a position other than the isocenter 31.

In the present embodiment, the table positional deviation d is calculated based on a scout image, but the table positional deviation d may be calculated based on a CT image acquired by a diagnostic scan.

In the present embodiment, after updating the offset, the table 116 is driven based on the updated offset. However, enabling the operator to make a selection and operate the operator console 220 (see FIG. 2) to enter operator input into the computer 216 to drive table 116 based on updated offsets or to drive table 116 based on pre-updated offsets is also feasible. Furthermore, the operator may be allowed to select for each imaging location whether to drive the table 116 based on the updated offset or drive the table 116 based on the pre-updated offset.

In the present embodiment, an X-ray CT device is exemplified as a medical device, and an example of offset correction is described. However, the medical device of the present invention is not limited to an X-ray CT device, and the present invention can be applied to a medical device where table height is adjusted using an offset (for example, MRI device, PET-CT device, PET-MR device).

The invention claimed is:

1. A medical device comprising:

a table on which a subject is placed; and at least one processor, wherein each time an examination of the subject is performed, the at least one processor executes operations including:

driving the table, using a table controller, based on an offset for correcting a table height positional offset to position an imaging location of the subject at a prescribed table height position, determining a center of gravity of the imaging location of the subject in a height direction of the table based on a medical image of the imaging location of the subject, and calculating a difference between a prescribed position and the center of gravity as positional deviation of table height, storing the positional deviation, obtaining a representative value representing characteristics of a positional deviation distribution, determining whether the representative value of the positional deviation is statistically reliable, and updating the offset based on the representative value if the representative value is determined to be statistically reliable; and wherein the medical device further includes an operator console enabling an operator to select whether to drive the table based on the updated offset or drive the table based on the offset prior to updating.

2. The medical device according to claim 1, wherein this determining determines whether or not a positional deviation representative value is statistically reliable based on a threshold for determining whether or not the positional deviation representative value is statistically reliable.

3. The medical device according to claim 2, wherein the threshold is calculated based on a degree of variation of the positional deviation.

4. The medical device according to claim 3, wherein the degree of variation is standard deviation or variance.

5. The medical device according to claim 4, wherein the threshold is 3 standard deviations.

6. The medical device according to claim 5, wherein the representative value is an average value, median value, or mode value.

7. The medical device according to claim 6, wherein storing the positional deviation includes storing the positional deviation associated with an imaging location.

8. The medical device according to claim 7, wherein a storing device includes storing the offset for each imaging location and the at least one processor drives the table using the table controller based on the offset corresponding to the imaging location of the subject.

9. The medical device according to claim 8, wherein the at least one processor executes an operation including determining an amount to move the table based on a camera image.

10. The medical device according to claim 1, wherein the table includes a cradle in which the subject can lie, the at least one processor executes determining a first movement amount of the table in a height direction based on an optical image of the imaging location of the subject and a second movement amount for the cradle in a body axis direction, and driving the table includes driving the table based on the offset, the first movement amount, and the second movement amount.

11. The medical device according to claim 1, wherein the at least one processor determines to not update the offset if the representative value is determined to not be statistically reliable.

12. The medical device according to claim 1, wherein the prescribed location is an isocenter.

13. The medical device according to claim 1, wherein the medical image is a scout image obtained by a scout scan or a CT image obtained by a diagnostic scan.

14. A method of driving a table on which a subject is placed and for each examination of the subject, executing:

driving the table based on an offset for correcting a table height positional offset to position an imaging location of the subject at a prescribed table height position, determining a center of gravity of the imaging location of the subject in a height direction of the table based on a medical image of the imaging location of the subject, calculating a difference between a prescribed position and a center of gravity as positional deviation of the table height, and storing the positional deviation;

the method of driving the table further comprising:

obtaining a representative value indicating characteristics of a positional deviation distribution;

determining whether the representative value of the positional deviation is statistically reliable, updating the offset based on the representative value if the representative value is determined to be statistically reliable, and driving, in response to input from an operator, the table based on the updated offset or drive the table based on the offset prior to updating.

15. A storing device, comprising:

a non-transitory computer-readable recording medium having stored thereon one or more instructions executable by at least one processor, and when executed by the at least one processor each time an examination of a subject is executed, the one or more instructions for executing operations include:

driving a table using a table controller for controlling the table based on an offset for correcting a table height positional offset to enable positioning an imaging location of the subject at a prescribed table height position, determining a center of gravity of the imaging location of the subject in a height direction of the table based on a medical image of the imaging location of the subject, calculating a difference between a prescribed position and the center of gravity as positional deviation of table height, and storing the positional deviation; and when executed by the at least one processor, the one or more instructions for executing operations further include:

obtaining a representative value representing characteristics of a positional deviation distribution, determining whether the representative value of the positional deviation is statistically reliable, updating the offset based on the representative value if the representative value is determined to be statistically reliable, and driving, in response to input from an operator, the table based on the updated offset or drive the table based on the offset prior to updating.

* * * * *